United States Patent
Rehder et al.

(10) Patent No.: US 6,755,199 B2
(45) Date of Patent: Jun. 29, 2004

(54) MAGNETIC SENSING PROBE ASSEMBLY AND METHOD

(75) Inventors: Carey D. Rehder, Woodbury, MN (US); Jason P. Porter, Mound, MN (US); Deron J. Singer, Burnsville, MN (US)

(73) Assignee: PMT Corporation, Chanhassen, MN (US)

(*) Notice: Subject to any disclaimer, the term of this patent is extended or adjusted under 35 U.S.C. 154(b) by 522 days.

(21) Appl. No.: 09/784,582

(22) Filed: Feb. 15, 2001

(65) Prior Publication Data

US 2002/0108623 A1 Aug. 15, 2002

(51) Int. Cl.[7] ................................................ A61B 19/00
(52) U.S. Cl. ...................................... 128/899; 128/898
(58) Field of Search ................................ 324/200, 235; 101/333; 128/899

(56) References Cited

U.S. PATENT DOCUMENTS

| | | |
|---|---|---|
| 3,845,384 A | 10/1974 | Stoutenberg et al. |
| 4,222,374 A | 9/1980 | Sampson et al. |
| 4,296,376 A * | 10/1981 | Bartol, Jr. .................. 324/235 |
| 4,671,255 A | 6/1987 | Dubrul et al. |
| 5,123,349 A * | 6/1992 | Beaver et al. .............. 101/333 |
| 5,146,933 A | 9/1992 | Boyd |

* cited by examiner

*Primary Examiner*—Henry Bennett
*Assistant Examiner*—Sabrina Dagostino
(74) *Attorney, Agent, or Firm*—Anthony G. Eggink

(57) ABSTRACT

A sensing probe assembly and method for locating a magnetic field emitted by an implanted medical device. The assembly has a housing containing a magnetic field sensor circuit having an indicator light and a magnetic switch. The assembly further has a structure for marking the location of the magnetic field. The method utilizes a marking system whereby at least four points forming at least two perpendicularly intersecting line segments are located and marked above the magnetic field. The intersection is then used as a reference point for performing a medical procedure on the implanted medical device.

23 Claims, 3 Drawing Sheets

MAGNETIC SENSING PROBE ASSEMBLY AND METHOD

BACKGROUND OF THE INVENTION

This invention relates generally to a magnetic sensing probe assembly and method for detecting and marking the location of an implanted medical device. Particularly, this invention relates to a magnetic sensing probe assembly and method for locating the source of a magnetic field emitted from an implanted medical device. The assembly and method provide for easily and conveniently locating the magnetic source in an implanted medical device and marking its location for purposes of conducting a medical procedure.

Related art devices have been found to be difficult to operate because of their physical dimensions, because they require sensory adjustments for various conditions or procedures, and/or because of their mechanical or antiquated design. The present invention overcomes the problems with the prior art and provides a convenient probe assembly for a user, for example a medical technician, practitioner, or physician, to precisely locate a magnetic material incorporated into or a magnetic field emanating from an implanted medical device and to physically mark the location of the magnetic material or field with a nonpermanent agent. Both the sensing and marking mechanisms are incorporated into the assembly.

It is an object of this invention to provide a sensing probe assembly constructed and arranged to locate magnetic material incorporated into or a magnetic field from a medical device or its components. Another object of the invention is to provide an improved sensing probe assembly which is accurate and easy to use. Another object of the invention is to incorporate a marking mechanism into the assembly so that the location of the magnetic material or field can be conveniently, physically, and nonpermanently marked. Yet another object of this invention is to provide a medical device which is compact, reliable, and economical.

SUMMARY OF THE INVENTION

This invention relates to a magnetic sensing probe assembly and method for detecting and locating an implanted medical device. The present invention is easily held in and controlled by one hand. The assembly comprises an elongated housing containing a light source or diode, a power source, a magnetic switch and a circuit for electrical connection between the light source and the magnetic switch. The housing has opposing ends, namely, a light end and a tip end.

The assembly of the present invention further has a marking means located on the tip end of the housing to mark the location of a source of a magnetic field on the tissue of a patient once the magnetic field has been detected. The magnetic source is accurately located by moving the magnetic sensing probe assembly across the area containing the medical device to establish two pairs of points above the source. The points are detected as locations where the light source illuminates as the magnetic switch detects a magnetic field. The points are marked by depressing the marking means on the patient's skin or tissue. The intersection of the line segments connecting the two pairs of points provides the precise location of the magnetic material or the magnetic field. This method can be used to locate a component of a medical device spatially aligned with the magnetic material or source, so that a medical procedure can then be performed on the medical device.

The present invention provides an assembly and method for using a magnetic sensing probe in an easy, quick, reliable and convenient manner to locate a source of a magnetic field and to mark its location, thereby marking the location of an implanted medical device, for example. Particularly the sensing probe assembly may be utilized to non-invasively locate an injection port of a tissue expander or implanted inflatable device to thereby permit the device to be filled with fluid.

These and other benefits of this invention will become clear from the following description by reference to the drawings.

DESCRIPTION OF THE PREFERRED EMBODIMENTS

The present invention relates to a magnetic sensing probe assembly and method which is useful for medical technicians, practitioners and physicians to locate and mark the source of a magnetic field which is incorporated into a medical device, for example. The invention provides for the quick, convenient and reliable marking of an implanted device in a non-invasive manner.

Figure 1:
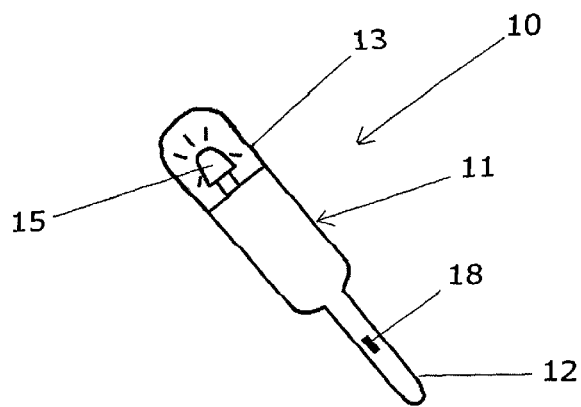
FIG. 1 is a lateral cross-sectional view of the probe housing of the magnetic sensing probe assembly of the invention.

FIG. 1 shows a lateral cross-sectional view of the magnetic sensing probe assembly 10 having an elongated housing 11 that encapsulates a magnetic switch 18, a light source or light-emitting diode (LED) 15, and a circuit for electrical connection between the magnetic switch 18 and LED 15. For example, the electrical circuit structure disclosed in U.S.

Figure 12:
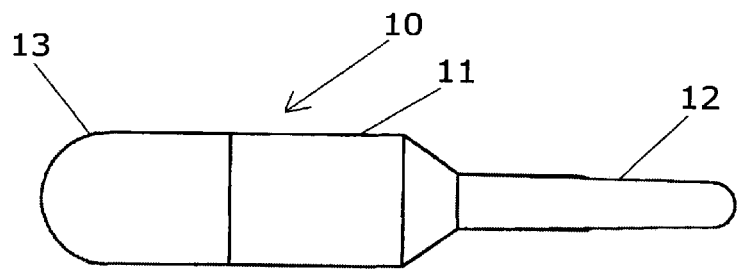
FIG. 12 is a plan view showing the probe housing of the sensing probe assembly.

Pat. No. 4,296,376 may be used to interconnect magnetic switch 18 and LED 15. Other circuits may also be used in accordance with the teachings of the present invention. The housing 11 has an elongated shape so that it may be conveniently held in one hand like a pencil and is preferably made of a nonmagnetic material. The housing 11 has a tip end 12 encapsulating the magnetic switch 18 and a light end 13 encapsulating the light-emitting LED 15, as shown in FIG. 12. The light end 13 of the housing 11 surrounding the LED 15 is transparent so that a user can clearly see when the diode or light source is illuminated. Optimally, the housing end 13 may be of a colored, transparent or translucent material, such as a polycarbonate or the like.

Figure 2:
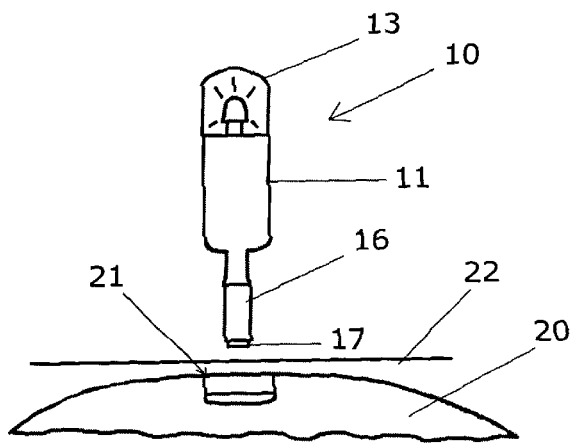
FIG. 2 is a lateral view of the magnetic sensing probe assembly being used to locate an implanted medical device.
Figure 3:
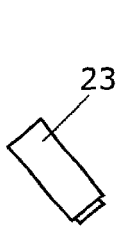
FIG. 3 is a lateral view of a marking cover having a circular marking tip.
Figure 4:
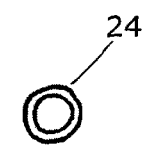
FIG. 4 is a bottom end view of the marking cover of FIG. 3.
Figure 5:
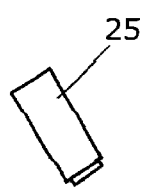
FIG. 5 is a lateral view of a marking cover having a square marking tip.
Figure 6:
FIG. 6 is a bottom end view of the marking cover of FIG. 5.
Figure 7:
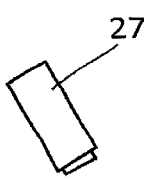
FIG. 7 is a lateral view of a marking cover having a triangular marking tip.
Figure 8:
FIG. 8 is a bottom end view of the marking cover of FIG. 7.
Figure 13:
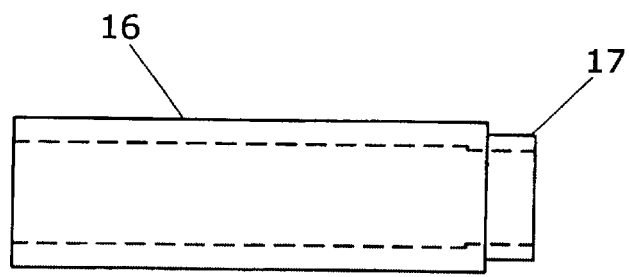
FIG. 13 is a plan view showing the marking cover of the sensing probe assembly.
Figure 14:
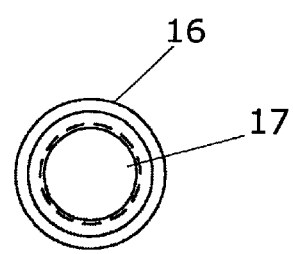
FIG. 14 is an end plan view of the marking cover of FIG. 13.

As shown in FIG. 2, the magnetic sensing probe assembly 10 enables a user to detect and physically mark the precise location of a magnetic material incorporated into an implant port 21 of an implanted medical device 20, for example. The magnetic sensing probe assembly 10 includes a marking cover structure 16 for marking the magnetic location on the skin or tissue 22 of a patient. The marking cover 16, further shown in FIGS. 13 and 14, is generally tubular in configuration and is constructed and arranged to fit over and hold onto the tip end 12 of the housing 11 encapsulating the magnetic switch 18. The marking cover 16 is preferably made of any nonmagnetic material, such as an acetal homopolymer composition or the like. The cover structure 16 has a marking tip 17 for physically marking the location of the magnetic implant port 21. The marking tip 17 is constructed so that it is held on the tip end 12 of the housing 11, and so that it can be depressed upon a patient's skin or tissue 22 to leave a nonpermanent physical mark thereon. The marking tip 17 is shown to have a peripheral indented portion which defines a geometric shape. While the marking tip may be of any shape or dimension, as shown in FIGS. 3-8, the cover tip is shown to have a geometric shape such as a circle 24, a square 26, or a triangle 28 which are shown on covers 23, 25 and 27, respectively. The physical mark may be created by the tip or by a marking agent, such as nonpermanent ink, that coats the marking tip 17 before it is pressed upon the patient. The marking cover 16 can be removed and reattached to the housing 11 as desired by the user or it may be permanently affixed to or incorporated into the housing 11. Both the housing 11 and marking cover 16 are of a material, as discussed above, which can be sterilized as required before using the sensing probe assembly 10 in a medical procedure.

Figure 9:
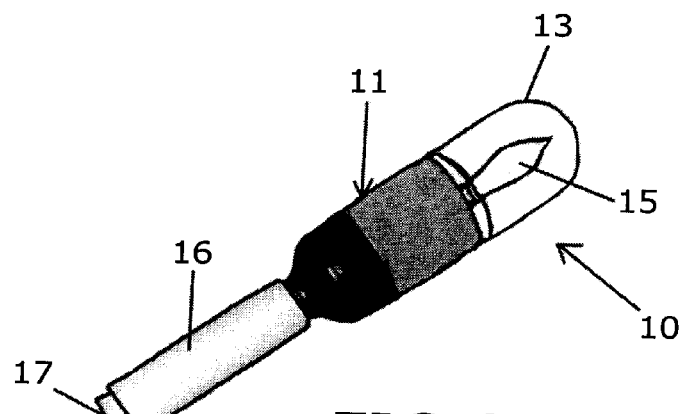
FIG. 9 is a perspective view of the magnetic sensing probe assembly of the present invention.
Figure 10:
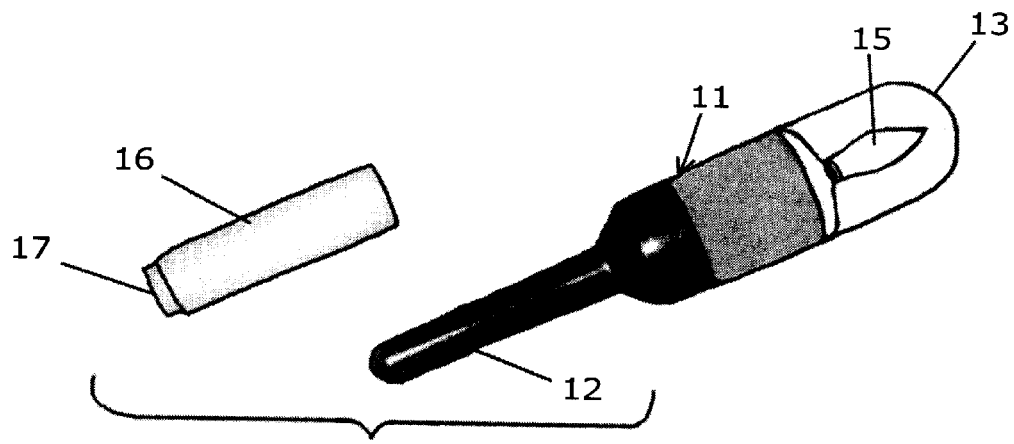
FIG. 10 is a perspective view of the magnetic sensing probe assembly of the present invention showing the assembly in a disassembled state.
Figure 11:
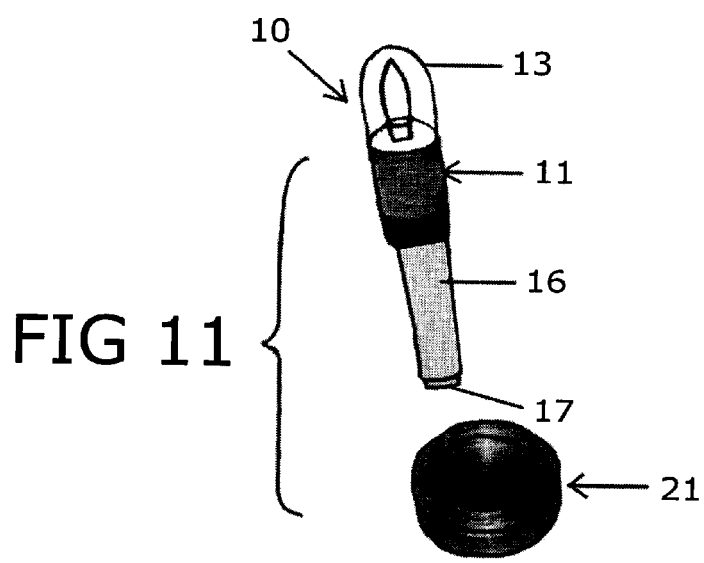
FIG. 11 is a perspective view of the magnetic sensing probe assembly in use with a magnetic implant port assembly.

FIG. 9 shows a perspective view of the magnetic sensing probe assembly 10, having light end 13, housing 11 and marking cover 16 with marking tip 17. FIG. 10 shows the marking cover 16 with marking tip 17 removed from magnetic sensing probe assembly 10, thereby showing the tip end 12 of housing 11. FIG. 11 shows the magnetic sensing probe assembly 10 in use with a magnetic implant port 21. Housing 11 is shown having light end 13 which illuminates when a magnetic material or field is sensed. Marking cover 16 with marking tip 17 can then be used to mark the location of the magnetic material.

An advantage of this invention is that a user can use the magnetic sensing probe assembly 10 with one hand to easily and quickly locate the precise location of the magnetic material or field. A medical device or component spatially aligned with the magnetic material, for example, an implant port may be located in a non-invasive manner. The location procedure is accomplished by using the assembly to detect and mark the periphery of the associated magnetic field, since both the sensing and the marking mechanisms are incorporated into a single, convenient design.

Figure 15:
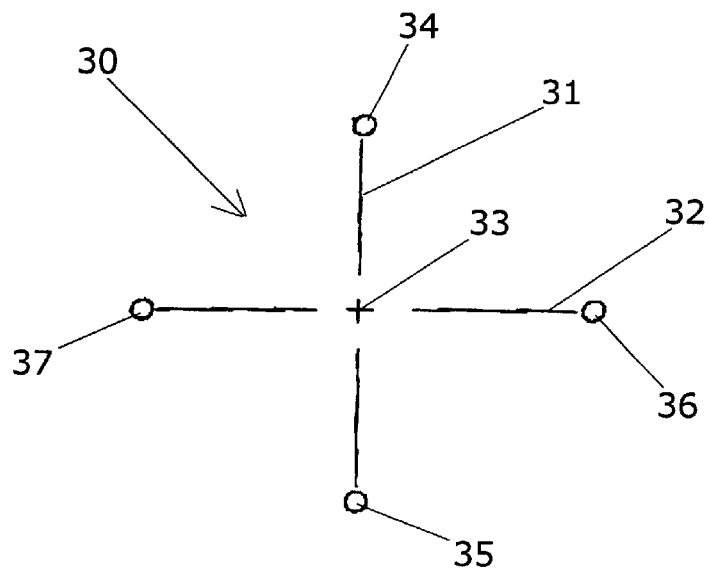
FIG. 15 shows the coordinate system used to locate an implanted medical device.

The method of the present invention uses the magnetic sensing probe assembly 10 to mark a coordinate system 30 on a patent's skin or tissue, as shown in FIG. 15. The probe assembly is scanned or moved across an area of the patient's skin or tissue under which the medical device is implanted. The magnetic material incorporated into the medical device produces a magnetic field which is detectable outside the patient's body. The magnetic switch activates and causes the light tip of the probe assembly to illuminate when it senses a magnetic field. When scanning the probe assembly across the area of skin the magnetic switch will activate when it senses a magnetic field and cause the light tip to illuminate, and will deactivate when it no longer senses the field, causing the light tip to darken. One sweep across the area will establish one point 36 where the light tip illuminates and another point 37 where the light tip illuminates. The marking tip can mark these two points 36 and 37 which establish a horizontal line segment 32. Upon sweeping the probe assembly perpendicular to the horizontal line segment 32 two more points 34 and 35 will become apparent where the light tip illuminates due to the magnetic switch sensing the magnetic field. These points 34 and 35 can be marked and establish vertical line segment 31. The intersection 33 of these two line segments 31 and 32 can also be marked and represents the location of the implanted medical device which is spatially aligned with a magnetic material or field. This location is where the medical procedure can be performed. More than two line segments and four reference points may also be detected and marked.

As many changes are possible to the embodiments of this invention, utilizing the teachings thereof, the description above and the accompanying drawings should be interpreted in the illustrative and not the limited sense.

That which is claimed:

1. A sensing probe assembly for detecting and marking the location of the source of a magnetic field emitted by an implanted medical device, said sensing probe assembly comprising:

a) a housing structure having an interior;

b) a magnetic field sensor circuit positioned in said interior of said housing structure, said sensor circuit further comprising an indicator light, a power source, a magnetic switch, and a means for connecting said light and said switch, wherein said switch is constructed and arranged to complete said circuit when said switch is exposed to a magnetic field;

c) a means disposed on the outside of said housing structure for marking the location of the magnetic field; and d) said housing structure and said means for marking being constructed of a sterilizable and durable plastic composition.

2. The assembly of claim 1, wherein said housing structure is nonmagnetic and elongated and has a tip end encapsulating said switch and a transparent light end encapsulating said indicator light.

3. The assembly of claim 2, wherein said means for marking the location of a magnetic field is a generally tubular marking cover constructed and arranged to fit over said tip end of said housing structure, wherein said marking cover is non-magnetic, and wherein said marking cover has a marking tip that can be depressed upon a patient's skin or other tissue to leave a nonpermanent physical mark thereon.

4. The assembly of claim 3, wherein said marking cover is removable from said housing structure.

5. The assembly of claim 3, wherein said marking tip of said marking cover has a geometric shape.

6. The assembly of claim 1, wherein said marking means is constructed and arranged to provide a mark of nonpermanent ink.

7. The assembly of claim 1, wherein said indicator light is a light-emitting diode and wherein said circuit includes a resistor.

8. A sensing probe for detecting and marking the source of a magnetic field comprising an elongated body containing a magnetic sensor, a switch, a power source and light emitting means, said body having an end with means to mark a target on the body of patient having an implanted device, said elongated body being constructed of a non-metallic sterilizable and molded material.

9. The sensing probe of claim 8, wherein said elongated body has opposing ends, one end being a tip end and the opposite end having said light emitting means.

10. The sensing probe of claim 9, wherein said tip of said probe body includes a tip cover having an end for marking the body of a patient and wherein said tip cover end is of a geometric shape.

11. The sensing probe of claim 8, wherein said power source in said probe body is a battery and said light emitting means is an LED.

12. The sensing probe of claim 1, wherein said elongated body is of a cylindrical structure, wherein said tip cover has means for providing a non permanent mark or impression.

13. The sensing probe of claim 8, wherein said elongated body has a removable tip cover constructed of material capable of sterilization and wherein said tip cover is constructed and arranged to mark the epidermal layer of a patient.

14. The sensing probe of claim 10, wherein said shape of said tip cover consists of a triangular, square or round configuration.

15. A process for detecting and marking the magnetic port of an implanted device on the skin of a patient comprising:
   a) providing a sensing probe according to claim 8, said sensing probe containing a magnetic sensor, a switch, a power source and light emitting means, said body having an end with means to mark a target on the body of patient having an implanted device;
   b) grasping said probe body and moving said probe body vertically and horizontally over the implanted device to locate the magnetic port; and
   c) locating the intersection of the coordinates and marking the intersection with said means to mark a target of said probe body.

16. A sensing probe for detecting and marking the source of a magnetic field comprising an elongated body containing a magnetic sensor, a switch, a power source and light emitting means, said body having an end with means to mark a target on the body of patient having an implanted device, said elongated body having a removable tip cover constructed of a sterilizable material, said tip cover further being constructed and arranged to mark the epidermal layer of a patient.

17. The sensing probe of claim 16, wherein said tip cover has an end having a geometric shape.

18. The sensing probe of claim 16, wherein said tip cover is constructed and arranged to provide a mark of non-permanent ink.

19. The sensing probe of claim 17, wherein said tip cover geometric shape consists of a triangular, square or round configuration.

20. The sensing probe of claim 16, wherein said sensing probe is constructed and arranged to detect and locate a magnetic element of an implanted medical device.

21. The sensing probe of claim 20, wherein said sensing probe is constructed and arranged to locate two intersecting lines to locate the magnetic element of the implanted medical device.

22. The sensing probe of claim 16, wherein said probe is constructed and arranged to detect the magnetic filling port of an implanted device.

23. The sensing probe assembly of claim 1, wherein said probe is constructed and arranged to detect the location of a magnetic element of an implanted medical device.

* * * * *